US009005286B2

(12) United States Patent
Giorno

(10) Patent No.: US 9,005,286 B2
(45) Date of Patent: Apr. 14, 2015

(54) PLGA/HA HYDROXYAPATITE COMPOSITE BONE GRAFTS AND METHOD OF MAKING

(71) Applicant: Thierry Giorno, Boca Raton, FL (US)

(72) Inventor: Thierry Giorno, Boca Raton, FL (US)

(73) Assignee: Thierry Giorno, Boca Raton, FL (US)

( * ) Notice: Subject to any disclaimer, the term of this patent is extended or adjusted under 35 U.S.C. 154(b) by 0 days.

(21) Appl. No.: 13/772,966

(22) Filed: Feb. 21, 2013

(65) Prior Publication Data

US 2013/0218291 A1 Aug. 22, 2013

Related U.S. Application Data

(60) Provisional application No. 61/601,281, filed on Feb. 21, 2012.

(51) Int. Cl.
A61F 2/28 (2006.01)
A61L 27/40 (2006.01)
A61L 27/46 (2006.01)
A61L 27/56 (2006.01)

(52) U.S. Cl.
CPC . A61L 27/40 (2013.01); A61F 2/28 (2013.01); A61L 27/46 (2013.01); A61L 27/56 (2013.01); A61L 2400/12 (2013.01); A61L 2430/02 (2013.01)

(58) Field of Classification Search
CPC ....................................... A61F 2/28
USPC ............ 623/16.11, 11.11, 23.6, 23.61–23.63, 623/23.75, 23.76, 23.55–23.59
See application file for complete search history.

(56) References Cited

U.S. PATENT DOCUMENTS

| 5,567,435 | A | 10/1996 | Hubbell et al. | |
|---|---|---|---|---|
| 5,567,440 | A | 10/1996 | Hubbell et al. | |
| 5,627,233 | A | 5/1997 | Hubbell et al. | |
| 5,628,863 | A | 5/1997 | Lee | |
| 5,654,381 | A | 8/1997 | Hrkach et al. | |
| 2003/0065400 | A1* | 4/2003 | Beam et al. | 623/23.51 |
| 2009/0254182 | A1* | 10/2009 | Kovarik et al. | 623/17.11 |
| 2011/0282465 | A1* | 11/2011 | Desai et al. | 623/23.61 |

OTHER PUBLICATIONS

De Boer, H. H., The History of Bone Grafts, Clinical Orthopedics and Related Research, 1998, pp. 292-298, 226.
Bonfiglio, M. et at., Immunological Responses to Bone, Clinical Orthopedics and Related Research, 1972, pp. 19-27, 87.
Coombes, A. G. A. et al., Resorbable Synthetic Polymers as Replacements for Bone Graft, Clinical Materials, 1994, pp. 35-67, 17.
Rizzi, S. C. et at., Biodegradable Polymer/hydroxyapatite Composites: Surface Analysis and initial Attachment of Human Osteoblasts, J Biomed Mater Res, 2001, pp. 475-486, 55.
Laurencin, C. T. et al., Advancements in Tissue Engineered Bone Substitutes, Current Opinion in Orthopedics, 1999, pp. 445-451, 10.

(Continued)

Primary Examiner — Jason-Dennis Stewart
(74) Attorney, Agent, or Firm — Keller Life Science Law, P.A.; Michael J. Keller

(57) ABSTRACT

The present invention involves tissue engineering constructs made from a new composite bone graft material made from biocompatible poly(D,L-lactic-co-glycolic acid) (PLGA) and bioceramic particles exposed on its surface using a gas foaming particle leaching (GF/PL) method and infused with collagen. Methods and apparatus for of forming scaffolds are also disclosed.

15 Claims, 14 Drawing Sheets

(56) References Cited

OTHER PUBLICATIONS

Ambrosio, A. M. A. at al., A Novel Amorphous Calcium Phosphate Polymer Ceramic for Bone Repair: I. Synthesis and Characterization. J Biomed Mater Res, 2001, pp. 295-301, 58.

Marra, K. G. et al., In vitro Analysis of Biodegradable Polymer Blend/hydroxyapatite Composites for Bone Tissue Engineering, J Biomed Mater Res., 1999, pp. 324-335, 47.

Wang, M., Developing Bioactive Composite Materials for Tissue Replacement, Biornaterials, 2003, pp. 2133-2151, 24.

Van Landuvt, P. et al., The Influence of High Sintering Temperatures On the Mechanical Properties of Hydroxyapatite, J Mater Sci: Mater Med, 1995, pp. 8-13, 6. (Abstract Only).

Khan, Y. M. et al., Novel Polymer-Synthesized Ceramic Composite-Based System for Bone Repair: An in vitro Evaluation, J Biomed Mater Res, 2004, pp. 728-737, 69.

Piattelli, A. et al., Resorption of Composite Polymer-Hydroxyapatite Membranes: A Time-Course Study in Rabbit, Biomaterials, 1996, pp. 629-633, 18.

Lu, L. et al., Synthetic Bone Substitutes, Current Opinion in Orthopedics, 2000, pp. 383-390, 11.

Peter, S. J. et al., Marrow Stromal Osteoblast Function on A Poly(propylene fumarate)/beta-tricalcium Phosphate Biodegradable Orthopaedic Composite, Biomaterials, 2000, pp. 1207-1213, 21.

Wei, G. et al., Structure and Properties of Nano-hydroxyapatite/polymer Composite Scaffolds for Bone Tissue Engineering, Biomaterials, 2004, pp. 4749-4757, 25.

Guan, L. et al., Preparation and Characterization of A Highly Macroporous Biodegradable Composite Tissue Engineering Scaffold, J Biomed Mater Res, 2004, pp. 480-487, 71.

Zhang, R. et al., Poly(alpha-hydroxyl acids)/hydroxyapatite Porous Composites for Bone-Tissue Engineering. I. Preparation and Morphology, J Biomed Mater Res, 1999, pp. 446-455, 44.

Lee, S. et al., Thermally Produced Biodegradable Scaffolds for Cartilage Tissue Engineering, Macromolecular Bioscience, 2004, pp. 802-810, 4.

Yang, S. et al., The Design of Scaffolds for Use in Tissue Engineering. Part I. Traditional Factors, Tissue Engineering, 2001, pp. 679-689, 7.

Jung, Y. et al., A poly(lactic acid)/calcium Metaphosphate Composite for Bone Tissue Engineering, Biomaterials, 2005, pp. 6314-6322, 26.

Jung, Y. et al., Tissue Engineered Bone Formation with Polymer/ceramic Composites by Press-and-Baking Method, Key Engineering Materials, 2005, pp. 79-82, 288.

Harris, L. D. et al., Open Pore Biodegradable Matrices Formed With Gas Foaming, J Biomed Mater Res, 1998, pp. 396-402, 42.

Cho, S. et al., Smooth Muscle-Like Tissues Engineered With Bone Marrow Stromal Cells, Biomaterials, 2004, pp. 2979-2986, 25.

Cho, S. et al., Engineering of Volume-Stable Adipose Tissues, Biomaterials, 2005, pp. 3577-3585, 26.

Kim, B. et al., Tissue Engineering of Smooth Muscle Under A Mechanically Dynamic Condition, J Microbiology & Biotechnology, 2003, pp. 841-845, 13.

Ekholm, M. et al., Tissue Reactions of Subcutaneously Implanted Mixture of epsilon-caproiactone-lactide Copolymer and Tricalcium Phosphate, J Mater Sci: Mater Med, 2003, pp. 913-918, 14.

Jaiswal, N. et at., Osteogenic Differentiation of Purified, Culture-Expanded Human Mesenchymal Stem Cells in vitro, J Cellular Biochemistry, 1997, pp. 295-312, 64.

Lewandrowski, K. et al., Enhanced Bioactivity of a Polypropylene fumarate) Bone Graft Substitute by Augmentation With Nano-hydroxyapatite, Bio-Medical Mater Eng, 2003, pp. 115-124, 13.

Ginebra, M. P. et al., Effect of the Particle Size on the Micro and Nanostructural Features of a Calcium Phosphate Cement: a Kinetic Analysis, Biomaterials, 2004, pp. 3453-3462, 25.

Burg, K. J. L. et al., Biomaterial Developments for Bone Tissue Engineering, Biomaterials, 2000, pp. 2347-2359, 21.

Akao, M. et al., Mechanical Properties of Sintered Hydroxyapatite for Prosthetic Applications, J Mater Sci, 1981, pp. 809-812, 16.

Anselme, K., Osteoblast Adhesion on Biomaterials, Biomaterials, 2000, pp. 667-681, 21.

Howe, A. K. et al., Anchorage-Dependent ERK Signaling—Mechanisms and Consequences, Current Opinion in Genetics & Development, 2002, pp. 30-35, 12.

Bigi, A. et al., Bonelike Apatite Growth on Hydroxyapatite-gelatin Sponges From Simulated Body Fluid, J Biomed Mater Res, 2001, pp. 709-715, 59.

Vandiver, J. et al., Nanoscale Variation in Surface Charge of Synthetic Hydroxyapatite Detected By Chemically and Spatially Specific High-Resolution Force Spectroscopy, Biomaterials, 2005, pp. 271-283, 26.

Lu, H. H. et al., Three-dimensional, Bioactive, Biodegradable, Polymer-bioactive Glass Composite Scaffolds With Improved Mechanical Properties Support Collagen Synthesis and Mineralization of Human Osteoblast-like Cells in vitro, J Biomed Mater Res, 2003, pp. 465-474, 64.

Li, H. et al., Preparation and Characterization of Bioactive and Biodegradable Wollastonitetpoly(D,L-lactic acid) Composite Scaffolds, J Mater Sci: Mater Med, 2004, pp. 1089-1095, 15.

Nayab, S. et al., Adhesion of Bone Cells to Ion-Implanted Titanium, J Mater Sci: Mater Med, 2003, pp. 991-997, 14.

Reis, R. L. et al., Bioenert, Biodegradable and Injectable Polymeric Matrix Composites for Hard Tissue Replacement: State of the Art and Recent Developments, Composites Science and Technology, 2004, pp. 789-817, 64. (Abstract Only).

Whitson, S.W. et al., Factors Influencing Synthesis and Mineralization of Bone Matrix from Fetal Bovine Bone Cells Grown in vitro, J Bone Miner Res, 1992, pp. 727-741, 7. (Abstract Only).

Stupp, S. I. et al., Organoapatites: Materials for Artificial Bone. I. Synthesis and Microstructure, J Biomed Mater Res, 1992, pp. 169-183, 26. (Abstract Only).

Kim, Sang-Soo, et al., Poly(lactide-co-glycolide)/hydroxyapatite composite scaffolds for bone tissue engineering, Biomaterial, 27, 1399-1409, 2006, available online Oct. 5, 2005.

Vacanti CA, Kim W, Upton J., Vacanti MP, Mooney D., Schloo B., et al., Tissue-engineered growth of bone and cartilage. Transplant Proc 1993; 25:1019-21. (Abstract Only).

\* cited by examiner

PLGA/HA HYDROXYAPATITE COMPOSITE BONE GRAFTS AND METHOD OF MAKING

This application claims priority to U.S. provisional patent application No. 61/601,128 filed on Feb. 21, 2012 and cross references and incorporates by reference patent application Ser. No. 12/279,172, PCT/US2007/05693, Ser. No. 12/279,172 and 60/767,137. The contents of all references, patents and patent applications are expressly incorporated by reference.

SUMMARY OF THE INVENTION

This invention is a novel biomaterial including formed shapes that are especially useful in tissue engineering applications involving bone. The composite comprises a polymeric scaffold, most preferably poly(D,L-lactic-co-glycolic acid) (PLGA) and particles of a bioactive bioceramic such as hydroxyapatite (HA), triCalcium phosphate (TCP), calcium sulfate or bioglass or a combination thereof, wherein the ceramic is highly exposed on the biomaterial surface. In one embodiment, a collagen solution is forced or infused through the biomaterial using pressure, centrigution or a vacuum. A further embodiment of this invention involves a ceramic, such as apatite, that is fastly, highly, and uniformly coated on the biomaterial surface. This new biomaterial is advantageous because it promotes bone cell propagation and ingrowth better than current materials. The biomechanical properties of this biocomposite in block form are far superior to hydroxyapatite blocks, or even to the natural bone. The material when milled is also suitable for use as a powder or granular material as a bone filler or cement, for filling spaces from a few $mm^3$ in volume to larger $cm^3$. Volumes of bone needing replacement can be measured using imaging technology and exact replacements produced through computer-aided design (CAD) in conjunction with computer aided manufacturing (CAM).

While PLGA scaffolds have been used in the past, such scaffolds were not optimal for the present applications because the porosity of the scaffolds made them degrade too quickly. HA blocks are widely available, but they are brittle and often break when anchored to the host bone with a screw. Following the methods and specifications described herein, one can fabricate scaffolds from PLGA which will be resident in the body long enough for the desired biological growth to occur before the biomaterial is absorbed by the body, yet provide immediate structural properties.

BACKGROUND

The ideal bone graft would replace bone defects, such as those from disease or trauma, with a material that allows bone cells to grow into the affected area, thus restoring the bone to its original condition. Currently, autografts are the best material for bone repair because they are biocompatible and there is little risk of disease transfer. However, the downside of autografts is that a separate operation must be performed to remove the person's own bone. Allografts, which consist of bone from another person/cadaver, as well as xenograft, (bone from another animal species) are also available but carry the risk of immune response and disease transfer that could lead to ultimate failure.

In order to solve the problems associated with bone grafts, many researchers have tried to develop artificial substances for bone grafts. These artificial biomaterials need to possess several qualities in order to be successful. First, the material must be porous to allow room for new bone to grow into the implant site. Second, it must maintain mechanical strength similar to native bone. Finally, the artificial biomaterial needs to be osteoconductive; that is, it must allow bone cells to attach and propagate on its surface, as it resorbs.

Some of the materials that have shown promise as bone grafts include calcium phosphate ceramics such as hydroxyapatite and tricalcium phosphate. These particular ceramics are quite biocompatible because they have characteristics similar to native bone mineral. However, they are hard to shape and do not possess the same mechanical properties as bone. They are quite brittle and require extremely delicate handling when shaping or drilling to avoid breaking the material. Hydroxyapatite degrades very slowly, which inhibits new bone from forming.

Another type of material that has sparked some interest is the use of degradable polymer. Polymers easy to shape and degrade at a predictable rate, thereby allowing new bone growth to replace it. Some examples of degradable polymers are poly(glycolic acid), poly(L-lactic acid), and poly(D,L-lactic-co-glycolic acid). Although they are easily formed and have good mechanical strength, degradable polymers alone are not ideal for bone grafts because they are not very osteoconductive. New bone will not attach well or grow well into this material.

Synthetic polymers which can be used in the present invention include poly(hydroxy acids) such as poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), polyanhydrides, polyorthoesters, poly(ester amides), polyamides, poly(ester ethers)polycarbonates, polyalkylenes such as polyethylene and polypropylene, polyalkylene glycols such as poly(ethylene glycol) (PEG), polyalkylene oxides such as poly(ethylene oxide) (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, polymers of acrylic acids, such as poly(methyl(meth)acrylate) (μmMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutylacrylate), poly(octadecyl acrylate) (jointly referred to herein as "polyacrylic acids"), and copolymers and mixtures thereof, polydioxanone and its copolymers, polyhydroxyalkanoates, poly(propylene fumarate), polyoxymethylene, and poloxamers.

The polymers can optionally include one or more photopolymerizable groups. The polymers can also be derivativatized. For example, the polymers can have substitutions such as alkyl groups, alkylene groups, or other chemical groups. The polymers can also be hydroxylated oxidized, or modified in some other way familiar to those skilled in the art. Blends and co-polymers of these polymers can also be used.

Preferred non-biodegradable polymers include ethylene vinyl acetate, polyacrylic acids, polyamides, and copolymers and blends thereof.

Preferred biodegradable polymers include poly(hydroxy acids) such as Poly lactic acid (PLA), poly glycolic acid (PGA), Poly lactic co-glycolic acid (PLGA), and copolymers with polyethylene glycol (PEG); polyanhydrides, poly(ortho) esters, polyurethanes, poly(butyric acid), poly(valeric acid), poly(lactide-co-caprolactone), trimethylene carbonate, and the polymers described in Hubbell et al., U.S. Pat. Nos. 5,654, 381; 5,627,233; 5,628,863; 5,567,440; and 5,567,435. In general, these materials degrade in vivo by both non-enzymatic and enzymatic hydrolysis, and by surface or bulk erosion.

Preferred water-soluble polymers include polyethylene oxides, polyethylene glycols, ethylene oxide-propylene oxide copolymers (poloxamers and poloxamines), polyvinyl alcohols, polyvinylpyrrolidones, poly(acrylic acids), and copolymers and blends thereof.

Natural polymers that can be used in the invention include polysaccharides such as alginate, dextran, and celluloses; collagens, including derivatized collagens (e.g., alkylated, hydroxylated, oxidized, or PEG-lated collagens, as well as collagens modified by other alterations routinely made by those skilled in the art); hydrophilic proteins such as albumin; hydrophobic proteins such as protamines, and copolymers and mixtures thereof. In general, these materials degrade by enzymatic hydrolysis, by exposure to water in vivo, or by surface or bulk erosion.

Preferred bioadhesive polymers include polyanhydrides and polyacrylic acids. In one embodiment, reactive groups on the polymers, for example, hydroxy, amine, carboxylic acid, thiol, anhydride, ester and vinyl groups are reacted with reactive groups on agents to be incorporated into the polymer matrix. For example, bioactive compounds such as proteins contain reactive amine groups which can be coupled with reactive carboxylic acid, ester, or anhydride groups on the polymer to form polymers that are covalently bonded to the compounds. In another embodiment, ion pairs are formed between acidic or basic groups on a polymer and basic or acidic groups on a bioactive compound to form a polymer that is ionically bonded to the compounds. Those of skill in the art can readily determine an appropriate bioactive compound and polymer to couple by forming ionic or covalent bonds, and can also readily determine appropriate reaction conditions for forming such bonds.

One factor to be considered when selecting an appropriate polymer is the time required for in vivo stability, i.e., the time in which the polymer matrix is required to degrade, in those embodiments in which the matrix is used in vivo. Preferably, the polymer matrix exhibits an in vivo stability between approximately a few minutes and one year. When used for drug delivery, the in vivo stability is preferably between a few hours and two months. When used for tissue engineering, the in vivo stability is preferably between one week and several months.

The art has used blocks of hydroxyapatite tri calcium phosphate (HA TCP) as a bone graft material. Such materials are extremely brittle and fracture when drilled or a screw is inserted. Additionally, HA TCP when used alone in blocks has limited porosity, if any, and tends to get encapsulated as a foreign body when implanted. As such, HA TCP Block is never truly integrated into the existing bone except at a very narrow margin at the surface of the block. As a result, it does not gain the strength of a graft fabricated from harvested bone.

It is possible to make a composite using a phosphate ceramic in conjunction with a degradable polymer. Small particles of ceramic can be included within the polymer scaffold material. These particles will be partially exposed on the surface of the biomaterial, thereby making the material more osteoconductive.

Most related methods for making a polymer/ceramic scaffold biomaterial use organic solvents. This can be highly disadvantageous because some residual solvent may remain in the material. Almost all organic solvents are detrimental to cell and tissue growth. Also, it has been noted that these processes may actually leave behind a thin film of polymer that coats the ceramic particles that are supposed to be exposed on the surface. This unintentional thin film disrupts the osteoconductive nature of the ceramic portion of these biomaterials.

Shaping polymer base scaffolds has presented significant challenges because the use of mechanical cutting and shaping devices such as drills or saws melts the polymer distorting the surface. In particular, the exposed hydroxyapatite is occluded rendering the material a less effective bone replacement. Conventional abrasives such as aluminum oxide or carborundum generally cannot be used because they will contaminate the scaffold.

The invention disclosed herein addresses the problems by describing a polymer/ceramic biomaterial comprised of degradable polymer and ceramic wherein the ceramic is highly exposed on the surface of the biomaterial and the biomaterial is fabricated with no use of organic solvents. The materials are infused with collagen, providing further attachment point for osteogenic cells. Furthermore, an additional layer of a mineral, such as apatite, can be coated on the surface of the biomaterial in an adherent, fast, uniform fashion. Finally, granules of the polymer/ceramic biomaterial with additional ceramic coating can be fabricated.

All references cited within this application are expressly incorporated by reference in their entirety.

BRIEF SUMMARY OF THE INVENTION

A preferred embodiment of the present invention is a biomaterial comprised of poly(D,L-lactic-co-glycolic acid) (PLGA), hydroxyapatite, and a possible coating of apatite. It is suitable as an artificial bone graft material. The said biomaterial is formed using a gas foaming method. GF introduces gas bubbles into the polymer matrix by saturating the polymer with gas at high pressure, and then reducing the pressure back to ambient conditions at a sufficiently fast rate to induce bubble formation. In a preferred embodiment $CO2$ gas is used, but any gas which is non-reactive with the biomaterial or its components may be used. In the present invention, hydroxyapatite serves as a porogen. Optionally, an additional porogen can be used to form pores, but such additional porogens have been found to created too much surface area in the PLGA leading to rapid degradation. Such additional porogens can be any biologically acceptable salt, gelatin, saccharose crystals or any other solid agent which can be solubilized in a solution which does not degrade PLGA or hydroxyapatite. While NaCl is a preferred salt, the salt particles can be any salt that can form crystals or particles having a diameter from 0.1 mm to 2 mm, which is easily removed from and does not react with the polymer, and is non-toxic if some residue remains in the polymer after leaching. Suitable salts include sodium salts, such as sodium chloride, sodium tartrate and sodium citrate, and other water soluble salts or compounds which remain insoluble in the polymer. Alternatively other particle forming agents which are capable of being washed out of the biomaterial may be used. Such agents can include proteins such as gelatin and agarose, starches, polysaccharides such as alginate and other polymers. In the preferred embodiment, pore forming particles are water soluble and leached out of the matrix using distilled water. Both gas foaming and particle leaching leave behind voids, which form the pores of this biomaterial matrix.

A preferred embodiment is made by combining particles of polymer and bioceramic, in certain ratios and then using the GF method. The size and amount of each particle will determine the general and interconnected porosity of the final biomaterial. Initially the polymer and bioceramic particles are sieved to obtain particles with a specific size. Then these particles are combined in certain ratios and loaded into a mold. The mixture is then exposed to high pressure CO2 gas (around 2000 psi) for 3-4 hours at a temperature of around 200 degrees F. It is believed that pressures as low as 400 psi and as high as 4000 psi will also work. During this time, the CO2 saturates the scaffold After 3-4 hours, the CO2 gas pressure is decreased to ambient pressure at a rate fast enough to induce nucleation and growth of CO2 bubbles, which form pores within the polymer scaffold portions of the biomaterial. If present, the optional sodium chloride particles are subsequently leached out of the material by immersing the scaffold in distilled water for a sufficient amount of time to dissolve the salt, thus leaving voids formerly occupied by the sodium chloride particles. While failing to remove the pore forming agent (salt) is not detrimental, more than one immersion in clean distilled water may be used to ensure removal of the pore forming particles. The final material is highly porous with bioceramic particles exposed on the surface of its polymer network.

The compositions are the present invention are collagen infused by placing them in a suitable vessel containing a solution of collagen and forcing the collagen into the pores via pressure, centrifugation or use of a vacuum. (negative pressure).

Furthermore, coating the surface of the polymer/bioceramic scaffold with a bone-like apatite using a biomimetic process can increase its osteogenic potential. This biomimetic process involves soaking the biomaterial in a solution of simulated body fluid (SBF) that has appropriate concentrations of ions dissolved in solution. Certain ions will precipitate on the surface of the biomaterial and form an apatite mineral coating.

In another embodiment, the polymer/bioceramic biomaterial may be ground up and sieved to collect granules with a certain size. These granules may then be soaked in the SBF and receive the apatite coating that enhances its osteogenic properties.

A bone graft material according to the present teachings can be provided in the form of a bone paste, a shaped solid, or a dry pre-mix useful for forming such a paste or solid. The phrase "bone paste" refers to a slurry or semi-solid composition of any consistency that hardens to form a solid structure, and thus includes, e.g., bone plasters, putties, adhesives, cements, bone void fillers, and bone substitutes. As a result, the bone paste can be any composition capable of being injected, molded, painted, suffused, or placed into contact with a bone surface in vivo. The "shaped solid" can take any form, including a pellet that can be placed into a bone void or into contact with a bone surface in vivo. The dry pre-mix can be provided in the form of a powdered and/or granular material.

In another embodiment, the biomaterial is further infused with nano collagen fibers by forcing a collagen solution through the biomaterial.

In another embodiment the biomaterial is shaped using CAD/CAM technologies to more precisely replicate a region of bone requiring replacement.

DETAILED DESCRIPTION OF THE INVENTION

Figure 1:
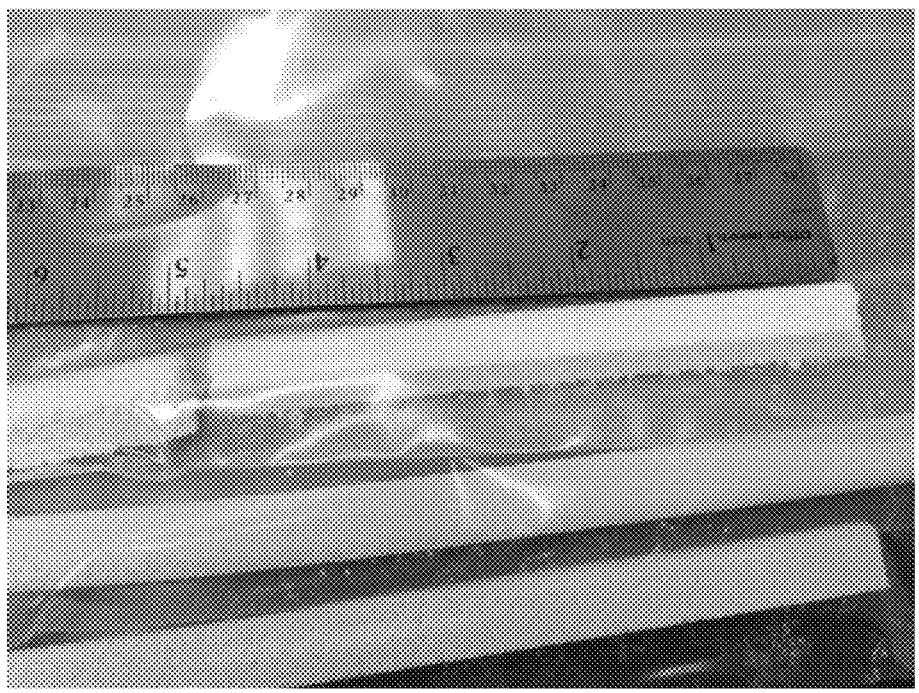
FIG. 1 is a black and white photograph of a bone graft of the present invention.
Figure 2:
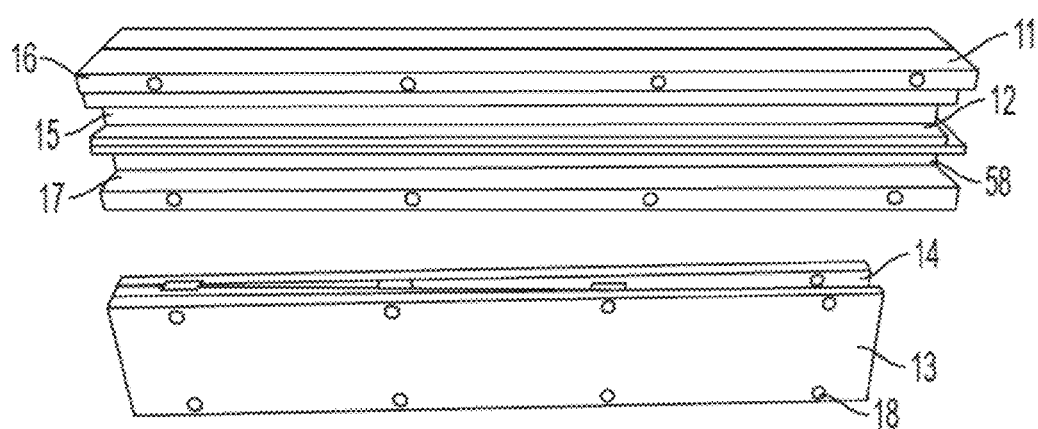
FIG. 2 is a drawing of a mold having a Teflon sheath inserted.
Figure 3:
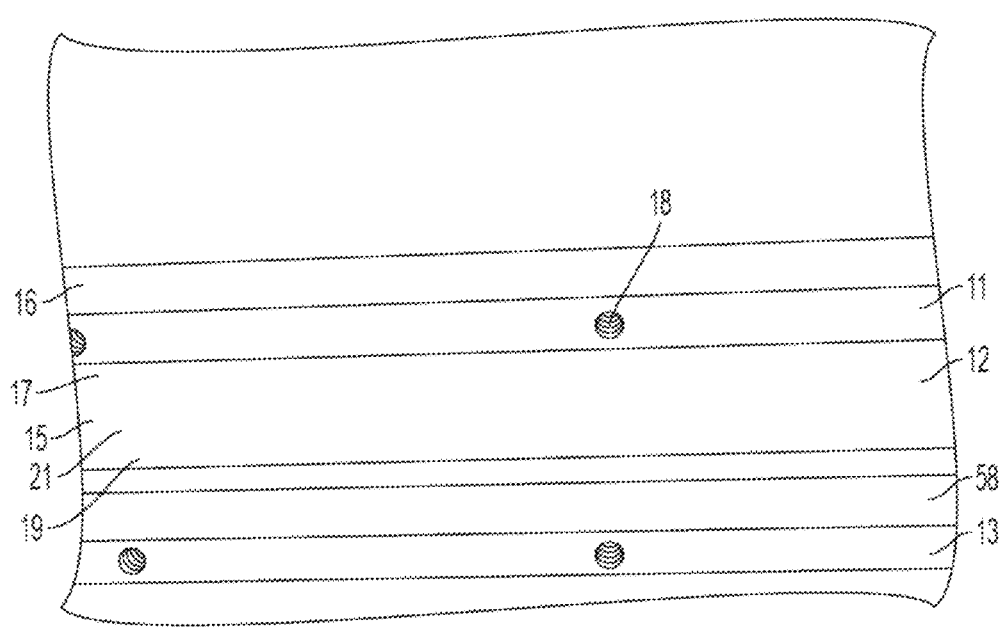
FIG. 3 is a top view of the mold showing Teflon sheath.
Figure 4:
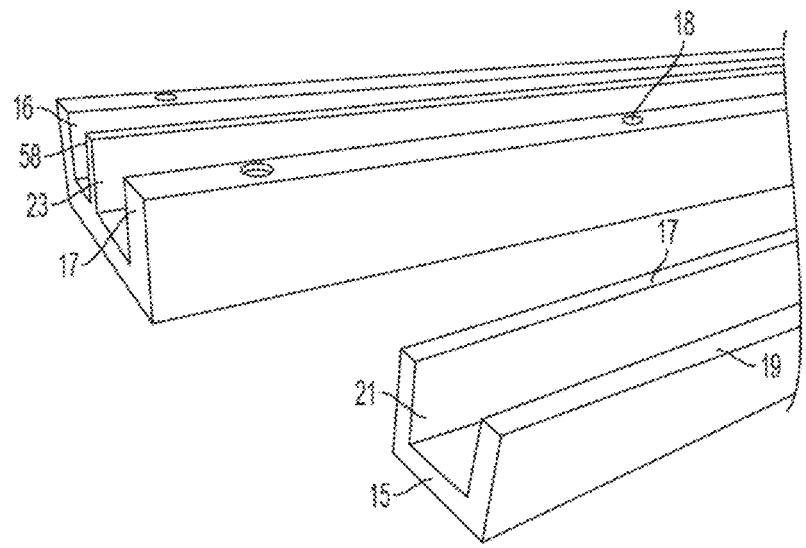
FIG. 4 is a drawing of the mold showing Teflon sheath removed.
Figure 5:
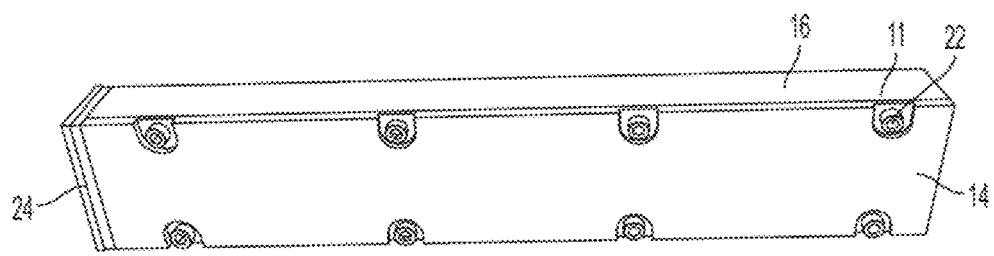
FIG. 5 is a top view of the assembled mold.

The present invention is a novel biomaterial with special characteristics that allow it to perform well as a bone graft material. It is comprised of a polymer scaffold, preferably a degradable poly(D,L lactic-co-glycolic acid) polymer with incorporated bioceramic particles and made by a gas foaming (GF) method. A further embodiment of this invention describes the same biomaterial infused with collagen and/or with an adherent, highly uniform apatite coating.

The method of constructing a PLGA polymer scaffold using GF/PL is described thoroughly in the journal article titled, "*Open pore biodegradable matrices formed with gas foaming*" (Harris L D, Kim B S, and Mooney D J; J Biomed Mater Res, 42, 396-402, 1998). This entire article is hereby incorporated by reference. The research reported in this article found that the porosity and pore size of the PLGA scaffold can be controlled by the salt/PLGA ratio and respective particle sizes. Also, the pores of the matrix are interconnected and highly uniform. In this manner, a useful scaffold can be created without the use of organic solvents or high temperatures. The present inventor has discovered that the particle leaching of Kim is not required to produce suitable pores and in fact products scaffolds that degrade too quickly due to excessive porosity.

While methods for constructing a polymer scaffold using GF are known, the use polymers with bioceramic particles as porogens in connection with high pressure gas foaming has not been taught in the prior art. Kim S S, Park M S, Jeon O, Choi C Y, and Kim B S; *Poly(lactide-co-glycolide)/hydroxyapatite composite scaffolds for bone tissue engineering*, Biomaterial, 27, 1399-1409, available online Oct. 5, 2005 describes the addition of nano hydroxyapatite particles to a PLGA scaffold. This article is also hereby incorporated by reference.

The most significant modification of the prior art methods is the omission of porogens which are washed out after scaffold formation and the infusion of collagen throughout the pores.

L-Lactide/caprolactone copolymer/HATCP composites were prepared with 75:25 Lactide/caprolactone copolymer particles (diameter=100-200 nm, molecular weight=100,000 Purac Biomaterials), HA TCP particles (diameter=approximately 100-1000 nm, 40% HA to 60% TCP). The polymer particles were mixed with the HA TCP particles. The PLGA/HATCP mass ratio ranged from 80:20 to 50:50 PLGA to HA by weight. The mixture was loaded into a mold and exposed to high pressure CO2 gas (2000 psi) for 3-4 hours to saturate the polymer with the gas. Temperature in the reaction vessel is maintained at around 200 degrees F. to maintain CO2 in the supercritical range. Then, decreasing the gas pressure to ambient pressure created a thermodynamic instability which led to the nucleation and growth of CO2 pores within the polymer scaffolds.

In a preferred embodiment the pressure is supplied by a reaction vessel 25. Referring to FIGS. 2-11, the reaction vessel 25 is preferably constructed out of stainless steel or other suitable material capable of withstanding the pressures recited herein. The vessel consists of a body 41 which defines a chamber 39. The chamber 39 is closed and sealed at one end and open on another end. In the figures the chamber is sealed with a bottom cap 28, which is bolted to a bottom flange 27 which is part of body 41. The open end is sealed by bolting a cap 31 which attached to a top flange 29 which is part of body 41. Gaskets or O-rings are used as required for sealing. Referring to FIG. 11 the caps and/or the flanges can include grooves 44 for one or more O-rings 45. While the photos show bolts used to hold the caps to the reaction vessel, any other means capable of handling the pressure may be used such as clamps, thumbscrews, etc.

A means is provided for increasing the pressure in the chamber 39. Such means can be externally mounted pumps 33 or pumps which are integrated into the reaction vessel. The vessel contains an inlet 34 which is connected to a manifold to control pressure in the chamber.

In the present embodiment, the pump 33 is connected via hose 35 to CO2 tank 41. The pump can be any pump suitable for pressurizing fluid or gas to the pressures recited herein. In the present embodiment the pump is a custom made pressure pump which is capable of generating pressures of between 2500-3000 psi. Such pumps are known in the art. The system includes a pressure gauge 32 for measuring pressure in chamber 39 in the reaction vessel 25. The pressure gauge 32 can be mounted anywhere suitable for measuring the pressure including the caps, body or input lines. In these Figures the pressure gauge 32 is mounted to the top cap.

Figure 6:
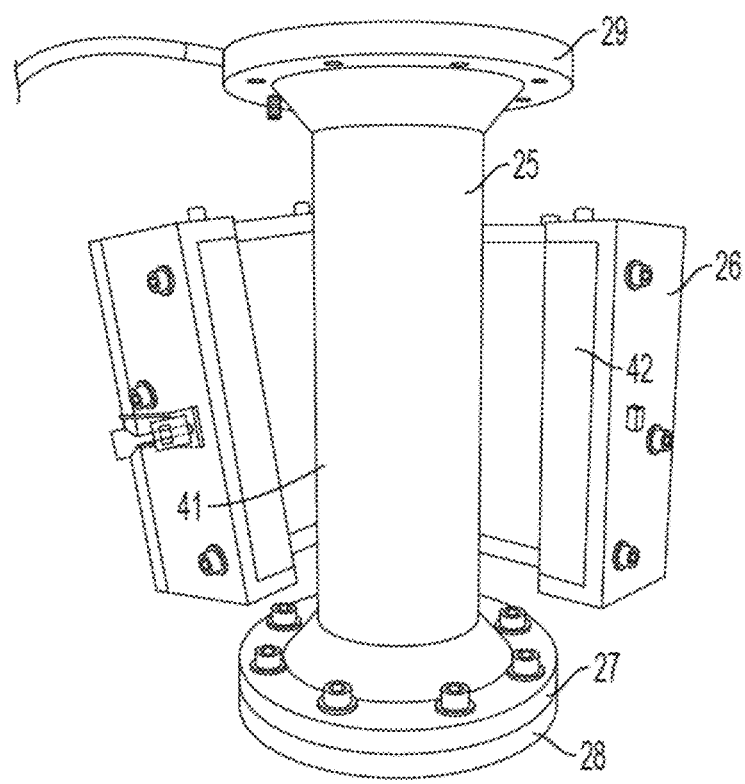
FIG. 6 is a side view of the reaction vessel.
Figure 7:
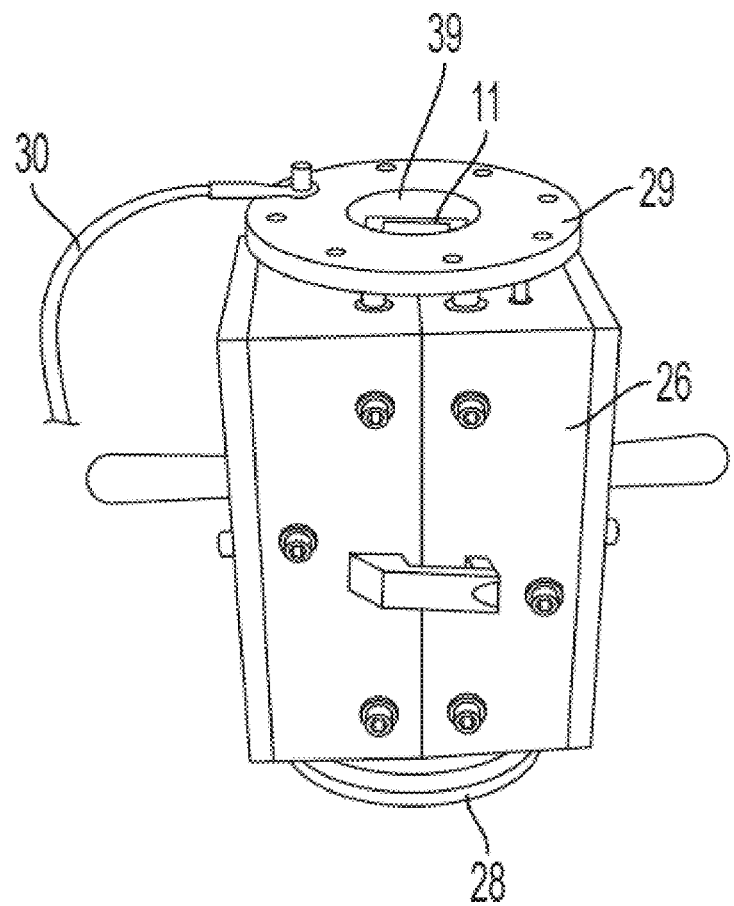
FIG. 7 is a side view of the reaction vessel with the secondary containment installed.
Figure 8:
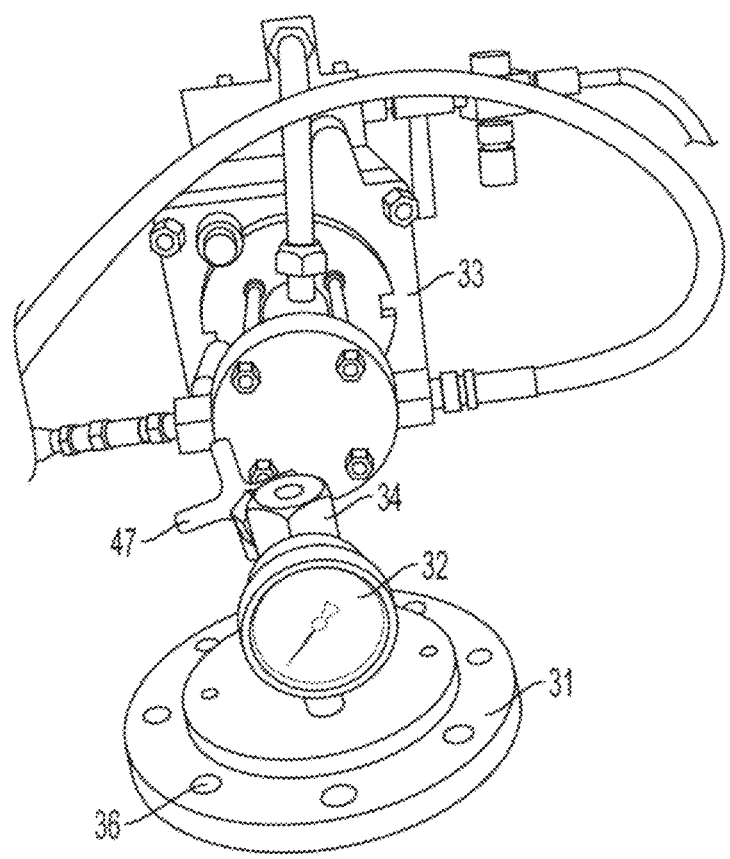
FIG. 8 is a drawing of the top of the reaction vessel cap and the pressure pump.
Figure 9:
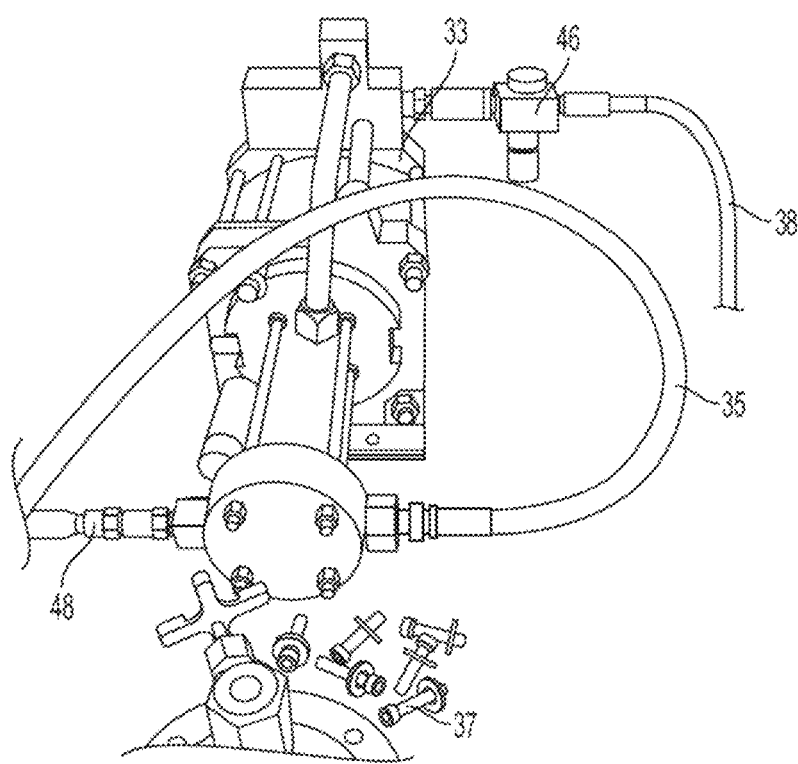
FIG. 9 is a drawing of the pressure pump.
Figure 10:
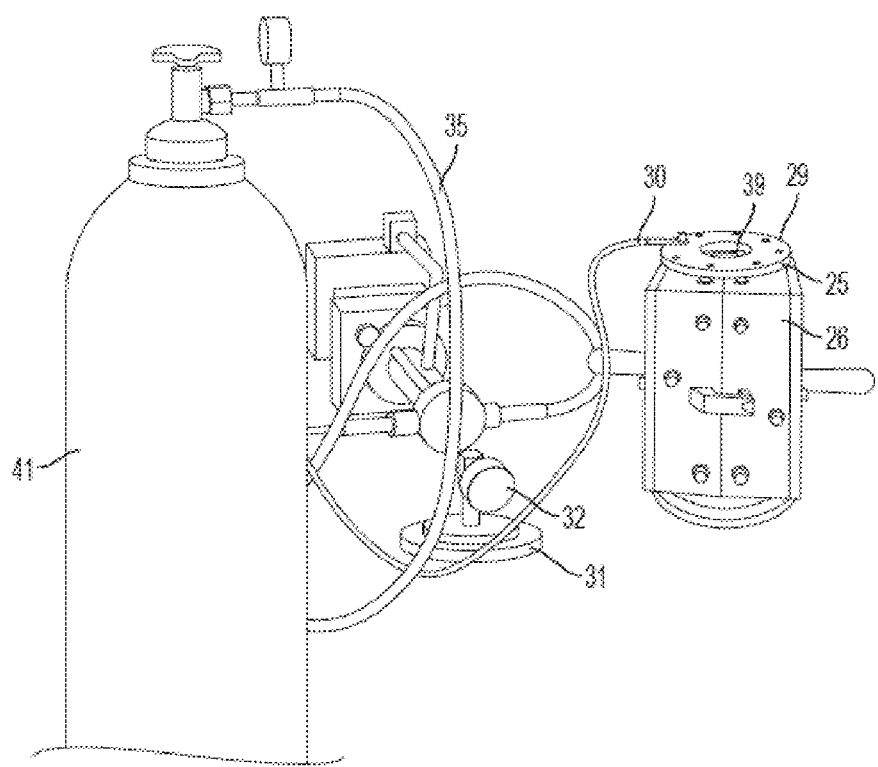
FIG. 10 is a drawing of the reaction system including the $CO_2$ tank.
Figure 11:
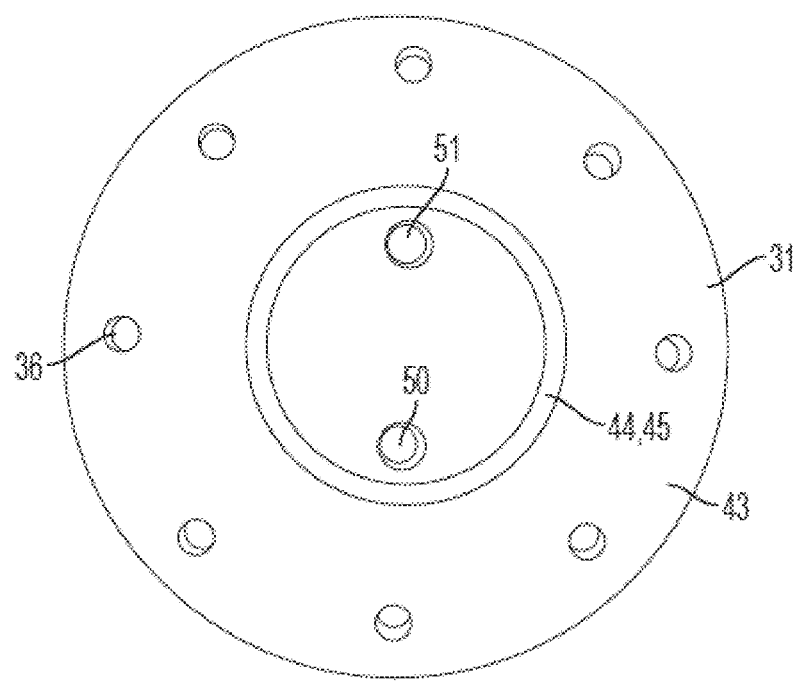
FIG. 11 is a bottom view of the reactor cap.
Figure 12:
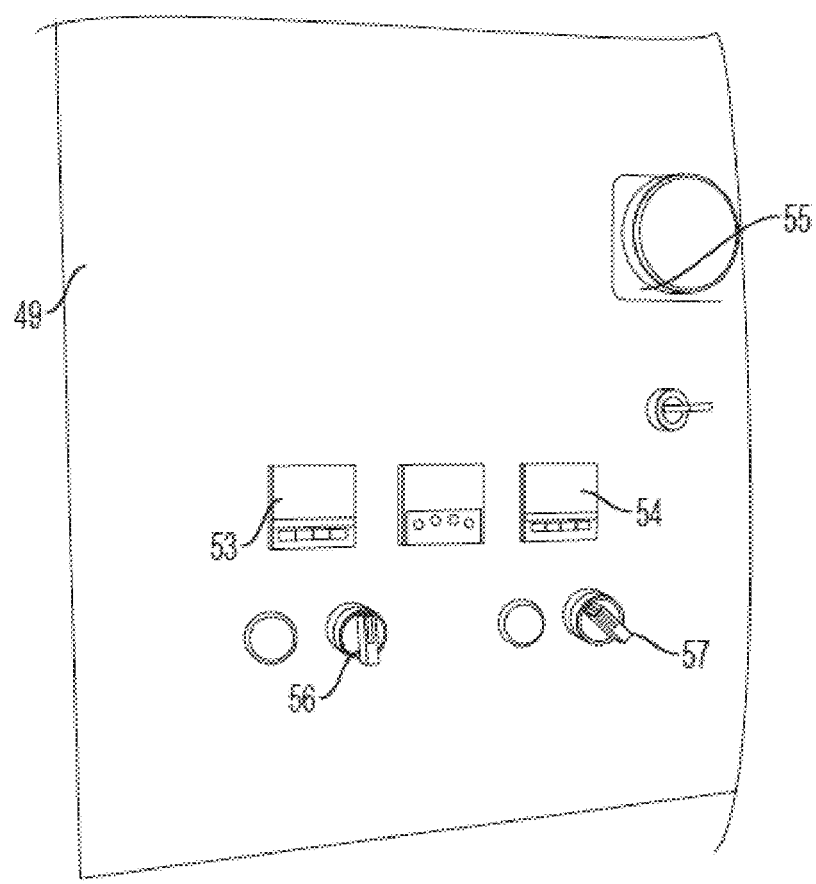
FIG. 12 is a view of the control panel.

Referring to FIGS. 6, 7 and 10, a secondary containment case 26 is provided around the reaction vessel 25 to hold the heating device.

The secondary containment case 26 also houses a heater 42 which is used to elevate the temperature in the reaction vessel 25. The heater is an electric resistance heating element capable of maintaining temperatures in the reaction vessel of around 200 degrees F. It is contemplated that other sources of heat could be applied in an industrial setting such as infrared, steam or heated water.

While the above materials are preferred, it is believed that the present invention will work with polymers of diameters from 50-500 μm and with bioceramic particles having diameters of 50-500 μm and salt particles having diameters from 50-300 μm. It is believed that the ratios of polymer to hydroxy apatite to NaCl can vary by as much as 50% without deviating from the spirit of this invention.

The process for creating these polymer/bioceramic composite biomaterials can be summarized by the steps of: (1) obtaining polymer in the appropriate particle size range (grinding small particles if necessary), (2) optionally sieving the polymer and bioceramic particles to yield particles with a 100-200 μm diameter, (3) mixing the particles of polymer and bioceramic in a mass ratio from about 4:1 polymer to bioceramic to about 1:1 polymer to bioceramic, (4) loading the mixture of particles into a mold, (5) compressing the mixture with a very high pressure CO2 gas long enough to saturate the disk, (6) decreasing the pressure on the disk until it returns to ambient pressure.

The rate at which pressure is vented from the reaction vessel determines the pore size. The faster the pressure release, the larger the pore size. It has been determined that decreasing the pressure to ambient over a period of 15-25 minutes yields desirable pore sizes. The faster pressure is released the larger the pore sizes. One of skill in the art will be able to determine the rate of release based on the specific composition of the scaffolds being produced.

Optionally, a further embodiment of the invention involves forming a uniform mineral coating of apatite on the surface of the polymer/bioceramic biomaterial. This apatite layer enhances the osteogenic potential of the biomaterial scaffold.

The apatite layer is created by incubating the bone graft in an ion rich simulated body fluid (SBF) solution. The solution is prepared by dissolving reagent grade NaCl, NaHCO3, Na2SO4, KCl, K2HPO4, MgCl2.6H2O, and CaCl2.2H2O in distilled deionized water. 1×SBF has the same ion concentrations as blood plasma while 5×SBF has ion concentrations five times greater than blood plasma. The pH is adjusted to 6.4 with tris(hydroxymethyl)aminomethane.

The described PLGA/hydroxyapatite biomaterial can be coated with apatite relatively quickly because the exposed hydroxyapatite particles act as nucleation sites for the growth of the mineral apatite layer in SBF solution.

A further embodiment of this invention involves the coating of PLGA/nanohydroxyapatite particles (rather than scaffolds) with a biomimetic, adherent, and uniform apatite coating. These particles will then be soaked in SBF solution to coat them with a uniform layer of biomimetic apatite.

Most of the previous methods for fabricating polymer/bioceramic composite scaffolds, such as the solvent casting and particulate leaching (SC/PL) method or the phase separation method, use organic solvents. However, residual solvents in the scaffolds may be harmful to transplanted cells or host tissues. Furthermore, the polymer coating on the ceramics created by polymer solutions may hinder the exposure of the ceramics to the scaffold surfaces, which could decrease the chance that osteogenic cells make contact with the bioactive ceramics.

The preferred embodiment of the present invention relies on gas forming (GF) methods to fabricate polymer bioceramic composite scaffolds for bone tissue engineering. This method efficiently exposes the bioceramic on the scaffold surfaces and avoids the use of organic solvents. Bioceramic particles used to fabricate the composite scaffolds are approximately 100 nanometers to 1000 microns in size.

Example 1

Process

L-Lactide/caprolactone copolymer/HA TCP composites were prepared with 75:25 Lactide/caprolactone copolymer particles (diameter=100-200 μm μm, molecular weight=100,000 Da, Purac Biomataerials), HA TCP particles (diameter=approximately 100-1000 nm, 40% HA to 60% TCP). The polymer particles were mixed with the HA TCP particles. The polymer/HA TCP mass ratio ranged from 80:20 to 50:50 polymer to HA TCP by weight. The mixture was loaded into a mold and exposed to high pressure CO2 gas (2000 psi) for 3-4 hours to saturate the polymer with the gas. Temperature in the reaction vessel is maintained at around 200 degrees F. to maintain CO2 in the supercritical range. Then, decreasing the gas pressure to ambient pressure created a thermodynamic instability which led to the nucleation and growth of CO2 pores within the polymer scaffolds.

The specific ratios of polymers is not critical, but plays a role in absorption. 50:50 ratios of co polymers tend to absorb faster. Changing the ratios from 50:50 can delay absorption by as much as 10%. The inventor has determined that Temperature in the reaction vessel is maintained at around 200 degrees F. to maintain CO2 in the supercritical range. Then, decreasing the gas pressure to ambient pressure created a thermodynamic instability. This led to the nucleation and growth of CO2 pores within the polymer scaffolds.

Figure 13:
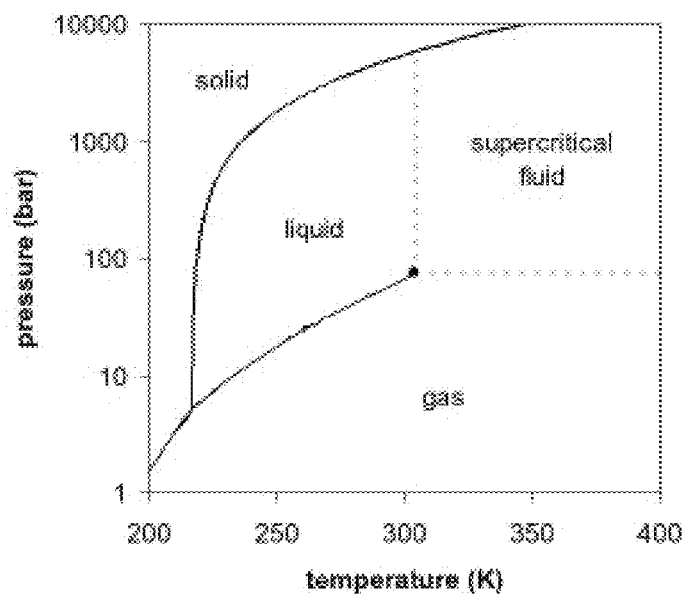
FIG. 13 is a CO2 phase diagram.

One of skill in the art will understand that temperature and pressure can be adjusted to yield a suitable product. Pressures can range from 400 to 4000 psi. The temperatures within the reaction vessel should equal or exceed the glass transition point for the polymers being used but should be below the temperature at which undesirable degradation of any materials in the reaction vessel occurs. It is preferred that the temperature and pressure be maintained such that the CO2 achieves a supercritical state. When in a supercritical state, substances are at a temperature and pressure above the thermodynamic critical point and have the ability to diffuse through solids like a gas, yet retain the ability to solubilize materials like a liquid. A representative phase diagram for CO2 is provided as FIG. 13.

In a preferred embodiment the pressure is supplied by a reaction vessel 25. Referring to FIGS. 2-11, the reaction vessel 25 is preferably constructed out of stainless steel or other suitable material capable of withstanding the pressures recited herein. The vessel consists of a body 41 which defines a chamber 39. The chamber 39 is closed and sealed at one end and open on another end. In the figures the chamber is sealed with a bottom cap 28 which is bolted to a bottom flange 27 which is part of body 41. The open end is sealed by bolting a cap 31 which attached to a top flange 29 which is part of body 41. Gaskets or O-rings are used as required for sealing. Referring to FIG. 10, the caps and/or the flanges can include one or more grooves for O-rings or seals. In a preferred embodiment, the seal is Teflon. While the photos show bolts used to hold the caps to the reaction vessel, any other means capable of handling the pressure may be used such as clamps.

A means is provided for increasing the pressure in the chamber 39. Such means can be externally mounted pumps 33 or pumps which are integrated into the reaction vessel. The vessel contains an inlet 34 which is connected to a manifold to control pressure in the chamber.

In the present embodiment, the pump 33 is connected via hose 35 to CO2 tank 41. The pump can be any pump suitable for pressurizing fluid or gas to the pressures recited herein. In the present embodiment the pump is a custom made pressure pump which is capable of generating pressures of between 2500-3000 psi. Such pumps are known in the art. The system includes a pressure gauge 32 for measuring pressure in chamber 39 in the reaction vessel 25. The pressure gauge 32 can be mounted anywhere suitable for measuring the pressure including the caps, body or input lines. In these Figures the pressure gauge 32 is mounted to the top cap.

Referring to FIGS. 6, 7 and 10, a secondary containment case 26 is provided around the reaction vessel 25. Such secondary containment is provided for added safety in the event of a rupture in the body of the reaction vessel. The secondary containment case can be fabricated out of any suitable material which can contain shrapnel from the reaction vessel in the event of a breach. Any suitable ballistics material can be used including, ballistics blankets, suitable metals such as stainless steel, aluminum, steel or alloys, composites such as fiberglass, carbon fiber or Kevlar, or polymers. In the present embodiment, the containment case 26 is made out of Teflon.

The secondary containment case 26 also houses a heater 42 which is used to elevate the temperature in the reaction vessel 25. The heater is an electric resistance heating element capable of maintaining temperatures in the reaction vessel of around 200 degrees F. It is contemplated that other sources of heat could be applied in an industrial setting such as infrared, steam or heated water.

While the above materials are preferred, it is believed that the present invention will work with polymers of diameters from 50-400 µm and with bioceramic particles having diameters of 150-1000 µm and optional salt particles having diameters from 50-300 µm.

The process for creating these polymer/bioceramic composite biomaterials can be summarized by the steps of: (1) obtaining polymer in the appropriate particle size range (grinding small particles if necessary), (2) optionally sieving the polymer and bioceramic particles to yield particles with a 100-200 µm diameter, (3) mixing the particles of polymer and bioceramic in a mass ratio from about 4:1 polymer to bioceramic to about 1:1 polymer to bioceramic, (4) loading the mixture of particles into a mold, (5) compressing the mixture with a very high pressure CO2 gas long enough to saturate the disk, (6) decreasing the pressure on the disk until it returns to ambient pressure.

The rate at which pressure is vented from the reaction vessel determines the pore size. The faster the pressure release, the larger the pore size. It has been determined that decreasing the pressure to ambient over a period of 15-25 minutes yields desirable pore sizes.

Optionally, a further embodiment of the invention involves forming a uniform mineral coating of apatite on the surface of the PLGA/hydroxyapatite biomaterial. This apatite layer enhances the osteogenic potential of the biomaterial scaffold.

The apatite layer is created by incubating the bone graft in an ion rich simulated body fluid (SBF) solution. The solution is prepared by dissolving reagent grade NaCl, NaHCO3, Na2SO4, KCl, K2HPO4, MgCl2.6H2O, and CaCl2.2H2O in distilled deionized water. 1×SBF has the same ion concentrations as blood plasma while 5×SBF has ion concentrations five times greater than blood plasma. The pH is adjusted to 6.4 with tris(hydroxymethyl)aminomethane.

The described PLGA/hydroxyapatite biomaterial can be coated with apatite relatively quickly because the exposed hydroxyapatite particles act as nucleation sites for the growth of the mineral apatite layer in SBF solution. Although the method for coating of polymeric biomaterial with apatite by incubating the biomaterial in SBF solution is already known, accelerated coating by incubating polymeric biomaterial with nano-hydroxyapatites exposed on the biomaterial surface has not been taught in the prior art.

Finally, the scaffolds were air-dried and then vacuum dried. The mass increase from apatite formation would be expressed as a percent increase compared to the scaffold mass when incubated in a tris-buffer at the same pH value, at the same temperature, and for the same time intervals.

The biomimetic apatite coating process is enhanced by introducing nano-sized hydroxyapatite nucleation sites and by using concentrated SBF solution. This coating is advantageous because it conveys better osteogenic properties to the polymer/bioceramic biomaterial.

A further embodiment of this invention involves the coating the scaffolds or powder with an adherent, and uniform apatite coating. The particles may be the product of a reaction process or be ground down from bulk polymer/bioceramic composite to a size of 30-2000 µm. The particles will be sieved to isolate particles with a more narrow size distribution depending on the desired application. These particles will then be soaked in SBF solution to coat them with a uniform layer of biomimetic apatite.

Most of the previous methods for fabricating polymer/bioceramic composite scaffolds, such as the solvent casting and particulate leaching (SC/PL) method or the phase separation method, use organic solvents. However, residual solvents in the scaffolds may be harmful to transplanted cells or host tissues. Furthermore, the polymer coating on the ceramics created by polymer solutions may hinder the exposure of the ceramics to the scaffold surfaces, which could decrease the chance that osteogenic cells make contact with the bioactive ceramics.

The preferred embodiment of the present invention relies on gas forming (GF) methods to fabricate polymer/bioceramic composite scaffolds for bone tissue engineering. This method efficiently exposes the bioceramic on the scaffold surfaces and avoids the use of organic solvents. To reduce the amount of bioceramic (HA degrades extremely slowly in vivo) required, and to increase the bioceramic exposure to the scaffold surface, bioceramic particles approximately 100 nm to 2 mm in size rather than micro-sized particles, are used to fabricate the composite scaffolds. The most preferred range of bioceramic particles is between about 150 μm to about 400 μm. The size of the particles depends in part on the rate of in vivo absorption. HA is known to absorb very slowly, whereas TCP and calcium sulfate are known to be absorbed faster. If HA is used alone, smaller particles are preferred, but when faster absorbing materials are used, larger particles are preferred.

The porosity of fabricated scaffolds can be measured using mercury intrusion porosimetry (Autopore IV 9500, Micromeritics Instrument Corporation, Norcross, Ga.). A contact angle of 1301 for mercury on the scaffold was used for this analysis. The pore structures of the scaffolds were examined using a scanning electron microscope (SEM, JEOL, Tokyo, Japan). Compression and tensile tests were performed with an Instron mechanical tester (Instron 4201, Instrons, Canton, Mass.). The scaffold samples are cut into 1×1 cm2 for compression testing. For tensile testing, the samples (1×1 cm2) can be attached to cardboard using epoxy glue. The sample can be centered in a 7 mm slot in the center of the cardboard and then glued to standardize the gauge length. Compression and tensile tests can be performed with a constant strain rate of 1 mm/min. The moduli can be determined from the slopes in the initial elastic portion of the stress-strain diagram. To examine the distribution and extent of surface exposure of HA in the scaffolds, the HA exposed to the scaffold surface can be visualized with a hydrophilic dye (trypan blue, Sigma) staining. The residual dye can be removed by sonication in 100% ethanol. Afterwards, the surface of the PLGA/HA scaffolds can be examined with a microscope (Camscope, Samtech, Seoul, Korea). To examine the chemical composition of the scaffold surface, one can carry out X-ray photoelectron spectroscopic (XPS; Sigma Probe, ThermoVG Scientific, West Sussex, UK) analyses, evaluating the O 1s, C 1s, Ca 2p, and P 2p peaks. The residual pressure in the spectrometer should be $1.1 \times 10^{-8}$ Pa, and a Mg anode (1.25 keV) powered at 250 W can be used as an X-ray source. The constant pass energy was 23 eV. All XPS data can be acquired at a nominal photoelectron takeoff angle of 551. The area of the XPS peaks can be determined after background subtraction, and the atomic percentage can be determined by normalizing the peak area of each element by the total peak areas of all elements.

Osteoblasts can be isolated from the calvaria of neonatal (less than one day old) Sprague-Dawley rats (SLC, Tokyo, Japan) by an enzymatic digestive process. The calvaria can be isolated, and all connective tissues were carefully removed. The parietal bones can be minced into pieces measuring about 1×1 mm$^2$ using sterile surgical scissors. Osteoblasts can be isolated by an enzyme solution containing 1.37 mg/ml collagenase type I (Sigma) and 0.5 mg/ml trypsin (Sigma). Following 30 min of incubation, the released cells are discarded to prevent contamination with other cell types. The minced bones are redigested with the enzyme solution for 30 min, and the supernatant is transferred to the culture medium, Dulbecco's Modified Eagles Medium (DMEM, Gibco BRL, Gaithersburg, Md.) containing 10% (v/v) fetal bovine serum (Gibco BRL), 1% (v/v) penicillin-streptomycin (Gibco BRL), 10 mM b-glycerophosphate (Sigma), 50 mg/ml L-ascorbic acid (Sigma), and 100 nM dexamethasone (Sigma). This process should be repeated three times, and then finally the collected solution is centrifuged for 10 min at 1500 μm. Cells are plated into tissue culture flasks and cultured in a humidified incubator at 37° C. with 5% (v/v) $CO_2$.

The fabricated scaffolds are sterilized by ethylene oxide gas and pre-wetted in the culture medium for 12 h. Aliquots of 50 ml of the cell suspension ($4.0 \times 10^7$ cells/ml, $2.0 \times 10^6$ cells/scaffold) are seeded onto the tops of the pre-wetted scaffolds. The scaffolds are left undisturbed in an incubator for 3 h to allow the cells to attach to the scaffolds. An additional 1 and 10 ml of culture medium are added to each scaffold at 6 and 8 h, respectively. The cell/scaffold constructs are cultured in a humidified incubator at 37° C. with 5% (v/v) $CO_2$ for eight weeks. The medium was changed every day. Analytical assays are performed at 7, 14, 28, and 56 days.

To determine the seeding efficiency and cell growth on the scaffolds, cell numbers are determined by quantitative DNA assays (n=3). DNA was isolated using a Wizard Genomic DNA Purification kit (Promega, Madison, Wis.). For DNA isolation, the cell/scaffold constructs are washed twice with phosphate-buffered saline. The specimens were placed in a 1.5-ml tube and crushed with a homogenizer (PowerGen 125, Fisher Scientific, Germany). DNA is isolated according to the kit protocol, and DNA content is measured with an ultraviolet absorbance spectrophotometer (JASCO V-530, Tokyo, Japan) at 260 nm. The cell numbers are calculated from a DNA standard curve of identical cells.

The alkaline phosphatase (ALP) production of osteoblasts cultured on scaffolds can be measured spectroscopically (n=3) using the methods of Ekholm M, Hietanen J, Tulamo R M, Muhonen J, Lindqvist C, Kellomaki M, et al. *Tissue reactions of subcutaneously implanted mixture of epsilon-caprolactone-lactide copolymer and tricalcium phosphate. An electron microscopic evaluation in sheep*. J Mater Sci Mater Med 2003; 14:913-8. The osteoblast/scaffold constructs are washed with PBS, homogenized with 1 ml Tris buffer (1 M, pH 8.0, Sigma), and sonicated for 4 min on ice. Aliquots of 20 ml are incubated with 1 ml of a p-nitrophenyl phosphate solution (16 mM, Sigma) at 301 C for up to 5 min. The production of p-nitrophenol in the presence of ALP is measured by monitoring light absorbance at 405 nm.

The amount of calcium deposited in the cell-scaffold constructs can be measured using a previously reported method (n=3) of Jaiswal N, Haynesworth S E, Caplan A I, Bruder S P. *Osteogenic differentiation of purified, culture-expanded human mesenchymal stem cells in vitro*. J Cell Biochem 1997; 64:295-312. After the cell-scaffold constructs are rinsed twice with PBS and homogenized with 0.6 N HCl, calcium is extracted by shaking for 4 h at 4° C. The lysate was then centrifuged at 1000 g for 5 min, and the supernatant is used to determine calcium content. To measure the amount of calcium produced by the seeded osteoblasts, the calcium content of the PLGA/HA scaffold itself is also measured, and the calcium content of the scaffold itself is subtracted from the total calcium content of the lysate. The calcium concentration in the cell lysates is quantified spectrophotometrically with cresolphthalein complexone (Sigma). Three minutes after the addition of reagents, the absorbance of the samples is read at 575 nm using a microplate reader (Multiskan Spectrum, Thermo Electron Co., Vantaa, Finland). The calcium concentration is calculated from a standard curve generated from a serial dilution of a calcium standard solution (Sigma).

The surface and cross-sectional morphologies of the scaffolds and cell-scaffold constructs can be examined using a SEM. The samples are washed twice with PBS, prefixed in 1% (v/v) buffered glutaraldehyde for 1 h, and fixed in 0.1% (v/v) buffered formaldehyde for 24 h. The fixed samples are dehydrated in ascending grades of ethanol, dried, and mounted on aluminum stubs using double-sided carbon tape. The specimens are coated with gold using a Sputter Coater (Cressington 108, Cressington Scientific Instruments, Cranberry, Pa.) and examined with SEM at an acceleration voltage of 10 kV.

In addition to the culture of cell-scaffold constructs in vitro, cell scaffold constructs can be implanted into the subcutaneous space of athymic mice (BALB/c-nu, 7 weeks old, female, SLC, Tokyo, Japan). After the mice are anesthetized with an intramuscular administration of ketamine hydrochloride (50 mg/kg, Yuhan Co., Seoul, Korea) and xylazine hydrochloride (5 mg/kg, Bayer Korea Ltd., Seoul, Korea), small incisions are made on the dorsal skins of six mice. Four pouches per animal are made by blunt dissection in subcutaneous sites, and cell-seeded scaffolds are immediately implanted into the pouches (n=4). Subsequently, the skin is closed with 5-0 Vicryl sutures (Ethicon, Lenneke Marelaan, Belgium). The mice are housed singly after surgery and received humane care in compliance with the Hanyang University Guidelines for the care and use of laboratory animals. The implants are retrieved for analysis at five and eight weeks after implantation.

The mechanical properties of the scaffolds can be assessed using compressive and tensile mechanical tests.

To determine whether the scaffold fabrication process affects the extent of HA exposure at the scaffold surface, the exposed HA can be stained with a hydrophilic dye. The surface composition of the PLGA/HA composite scaffolds can be analyzed with XPS.

First, the GF process avoids the use of organic solvents. Residual organic solvents remaining in scaffolds may damage transplanted cells and surrounding tissues. Furthermore, exposure to organic solvents may inactivate biologically active factors. Therefore, the GF process may cause less denaturation of the growth factors incorporated within the scaffolds.

Second, the GF method can efficiently expose bioceramics at the surface of the polymer/bioceramic composite scaffolds. Staining with a hydrophilic dye and XPS analysis would show that the GF method exposed a significantly higher extent of HA at the scaffold surface than did the conventional SC/PL method. Therefore, a GF scaffold can increase the chances of osteogenic cells to make contact with the bioactive ceramics, which enhances osteoblast differentiation and growth.

Figure 15:
FIG. 15 is a close black and white photograph of the block form of the present invention.

FIGS. 1 and 15 are photographs of the bone graft in block form.

Example 2

Powder

Figure 14:
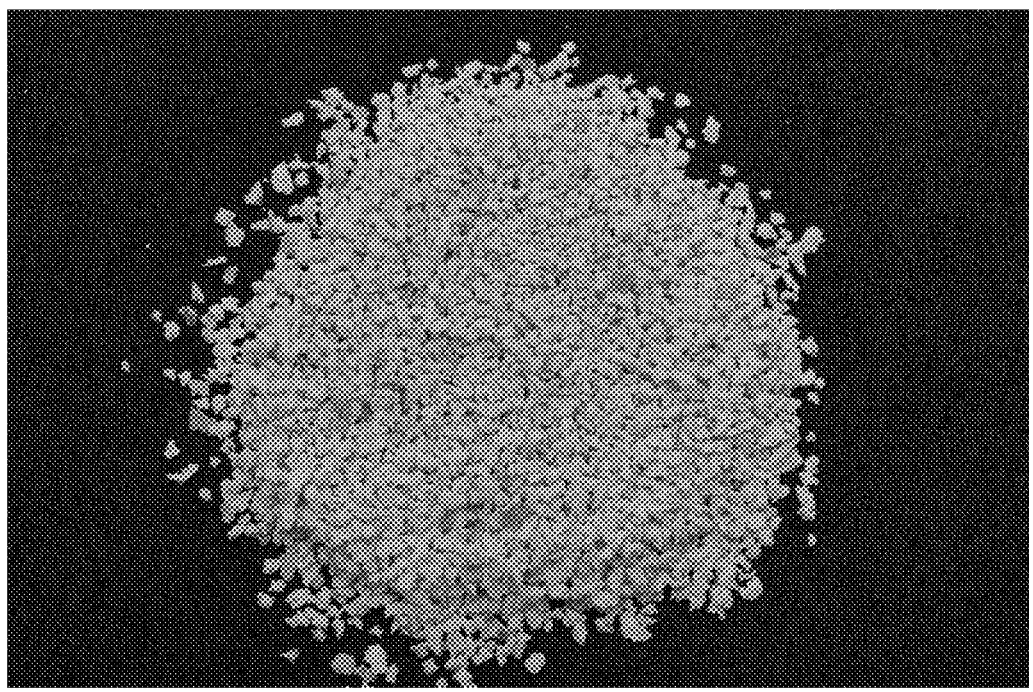
FIG. 14 is a close black and white photograph of a powder form of the present invention.

PLGA/HA scaffolds were created using the process of Example 1 and were ground to a powder sized between about 250 nm and about 2 mm. Most preferable the powder is graded into two different sizes of particles, the smaller consisting particles between about 250 nm and about 750 nm and the larger being between about 750 nm and about 2 mm. The resultant material can be used to pack surfaces around devices implanted in bone and packed in voids in bone to induce new bone growth. FIG. 14 is a photograph of the bone graft in powder form.

Those of skill in the art are familiar with the use of bone graft materials. The present invention can be used in the same manner as any other bone graft material. In a preferred delivery system, the bone graft material is mixed with polyethylene glycol or another hydrogel to form a paste. The material can be premixed and sold in a syringe for easy application or can be mixed at the point of use and delivered via any convenient means. When provided in a dry state, any suitable biocompatible fluid can be used to wet the material and create a paste for administration to the patient. Examples of such biocompatible fluid wetting agents include, but are not limited to: dextrose, glucose, maltose or sodium chloride solutions, blood, serum, platelet concentrate, bone marrow aspirate, and synovial fluid. A biological fluid can be used in the form obtained from the biological source, or it can be processed by application of one ore more desired useful techniques, examples of which include, separation techniques, such as filtration (macro-, micro-, or ultra-filtration); purification techniques, such as dialysis; concentration techniques; and sterilization techniques.

One of skill in the art will recognize that other biological components including but not limited to proteins, growth factors, cells, stem cells, osteoblasts or such other components that will promote bone growth or maturation of the bone graft.

Example 3

Molded Bone Grafts

The scaffold of Example 1 can be molded into a rigid implantable bone graft material of desired shapes by creating an appropriate mold for use in the reaction vessel. Referring to FIG. 2-7, the mold 11 consists of a bottom 40 and a right side 16 and a left side 17 which define a void 23. End caps 24 are placed at each end and a top cap 14 closes the mold. The shape of the void 23 determines the final shape of the bone graft 10. The mold can be designed to produce a single implant or can be designed to produce multiple implants. In the figures the mold contains a divider for producing two implants. One of skill in the art will appreciate that the mold can be designed to create bone grafts having complex shapes as well as simple geometric shapes. In the Figures, the molds are assembled using screws 22 although clamps or shaping the mold so it is evenly supported in the pressure vessel can also be used. When screws 22 are used, the top cap 14 and end caps 24 will have holes 18 drilled in them which correspond with threaded holes 18 in the right and left sides of the mold. Production molds 11 would be shaped to produce bone grafts 10 which roughly correspond to the shapes of bones to be replaced to reduce the amount of additional shaping required for use. When molded in this fashion, the need for further processing of the bone graft 10 is reduced or even possibly eliminated depending on the final use of the bone graft 10.

Example 4

Teflon Sheeths

Because of the extreme pressures generated in the reaction vessel 25, the scaffolds 10 in Example 1 expand making extraction of the rigid scaffold 10 extremely difficult. Additionally, there were signs of metal contamination of the bone graft material. To overcome these problems Teflon sheaths 11 were designed to facilitate removal. Referring to FIG. 2-7, the sheaths 11 can also be designed in a way to allow the scaffold to be molded during production. The Teflon material expands under pressure in the mold and shrinks back to its original shape when brought back to ambient temperature making it easy to remove the bone graft from the mold. Additionally the Teflon prevents contamination of the bone graft with the metal of the mold. When molded in this fashion, the need for further processing of the scaffolds is reduced or even possibly eliminated depending on the final use of the scaffold.

Scaffolds were formed using the process of Example 1 and the molds of Example 3 using a sheath 11 made of Teflon to line the reaction vessel 25 to facilitate removal of the scaffolds after production. The sheath 11 is machined or molded from Teflon and comprises a bottom 15, a right side 20 and a left side 19 which define a void 21 for receiving the scaffold material, and a liner cap 13. The sheath fits inside the mold 11.

In use, the sheath 12 would be placed inside the mold 11, filled with the bone graft material and the mold closed before being placed in the reaction vessel.

Example 5

Water-Jet Cutting

PLGA melts at a relatively low temperature. When cut with conventional cutting implements, the friction of the cutting surface causes the graft to melt destroying the pore structure. As such conventional toothed saws, rotary cutting instruments and drills cannot be used to shape the material without destroying its properties. Water cooled tools do not reduce the heat fast enough at the point of contact with the tool to prevent melting. This has been a serious impediment to shaping PLGA based materials. The problem has been overcome by using waterjets with or without an abrasive to perform the cutting.

The use of conventional cutting agents such as aluminum oxides or carborundum is to be avoided in implants because they will contaminate the implant. As a result, a non-conventional cutting agent had to be used. The inventor has discovered that HA is a suitable cutting agent and avoids the contamination issues of other cutting agents. The only size limitation on HA particles is the particle size limits of the equipment being used.

Waterjets are commonly used in the art and can be hand held or part of multi axis routers.

Scaffolds manufactured as in Examples 1 and 2 were cut into desired shapes using a waterjet using hydroxyapatite in the water as a cutting aid.

Example 6

Collagen Impregnation

Bone grafts manufactured and shaped according to Examples 1-3 were impregnated with collagen by forcing a collagen solution under pressure into the scaffold. The collagen can be from any source which would not render the bone graft unfit for its intended use. While common sources include pig, cow, and rat, human collagen is most preferred. Suitable collagen can be purchased commercially from companies such as Sunmax under the trade name Porcogen. Such collagen is sold as a solution of approximately 0.01 N HCl at a concentration of about 3 mg/ml. The stock solution is diluted by addition of approximately 9× phosphate buffer or cell culture media and the pH adjusted to approximately 7 by titration with 0.1N NaOH and/or 0.1N HCl. Encoll Corporation is another collagen supplier.

In another preferred embodiment the collagen is recombinant human collagen. Recombinant collagen potentially avoids contamination or purity issues which may exist with collagen processed from animal or human sources. A source of recombinant human collagens are FG-5016 and/or FG-5030 from Fibrogen Corporation. FG-5-16 is a recombinant human collagen where FG-5030 is a cross linked recombinant human collagen.

The collagen solutions should be between 0.1% and 10% with the most preferred range between approximately 2% and 5% collagen by weight in the solution.

In one embodiment the collagen is infused in the bone grafts by placing the bone graft in a centrifuge tube, adding the collagen solution and centrifuging at the equivalent RCF of 5000 g or higher for 10 minutes. This produces an acceptable degree of collagen distribution in the bone graft.

In another embodiment collagen is forced into the bone graft using pressure. In this embodiment the bone grafts are removed from the reactor and their sheaths and inspected. Optionally, the grafts can be further shaped at this time. The bone grafts were then placed into a vacuum chamber and placed under a vacuum. A preferred device is a commercial lyophilizer used to freeze dry. The vacuum is maintained until the moisture level is reduced to between 20% and 3% with 5% being a preferred target.

Example 7

Bone Graft Modeling

The bone grafts 10 of the present invention can be engineered to precisely replace damaged bone using CAD/CAM processes. In a first step, a patient needing bone replacement undergoes imaging to measure the region needing replacement. The measurements can be made using any suitable imaging technology from which three dimensional measurements can be taken, but at the present time computer aided tomography (CAT) scanning is the preferred method. Cone Beam Computerized Tomography, (CBCT) is a good alternative. Magnetic Resonance Imaging (MRI) is a potential alternative.

The dimensions of the bone defect to be reconstructed obtained from imaging software are exported into a solid file. (.stl, .igs or any other solid file format used in the industry). This solid file is loaded into the CAD software. The CAD software can then be used to design a mold suitable for use within the reaction vessel and/or to design a scaffold which can be cut using computer aided manufacturing technology. In some instances a mold may be sufficient to produce a final shape. In other situations, further shaping of the materials may be required. The scaffolds (molded or otherwise) can be shaped on a multi axis router. Because the polymers of the scaffolds can melt if exposed to a source of heat, the cutting heads need to be cooled. In a most preferred embodiment the cutting is performed using a waterjet, preferably with the use of hydroxyapatite particles as a cutting abrasive.

The resulting bone grafts 10 would be processes for storage and shipping as is customary in the art. Such processing steps include, but are not limited to, freeze drying, packaging and sterilization.

The resultant shaped bone graft 10 would then be implanted by a surgeon into a patient following removal of the area of damaged bone. The damaged bone can be removed to fit the bone graft or the bone graft can be further shaped by the surgeon using common cutting tools or abrasives to fit the damaged area.

Example 8

Spinal Fusion

Bone grafts of the present invention may be used for spinal fusion, a process in which two or more vertebrae are connected together. Traditional, surgeons place screws in each of the vertebrae to be fused together and connect them with plates or rods to prevent movement. Bone is preferable grafted in between the vertebrae to facilitate faster fusion. The grafts of the present invention can be shaped to more readily fit between vertebrae. The present invention facilitates faster fusion of the vertebral segments than using harvested bone.

The pores of the present invention also offer the ability to seed the bone graft with stem cells or biological agents. In one instance, the scaffold could be seed with cells to regrow cartilage and or ligaments. While such an implant would initially be rigid and unyielding, because the PLGA is slowly resorbed eventually the implant would gain the cushioning and flexibility of a normal disc.

Example 9

Bone Graft Kits

Because exact shape matching of an bone graft 10 to the region of bone to be replaced may be difficult prior to surgery, a kit can be created having various sizes of bone grafts. The bone graft selection can be made by the surgeon during the procedure. Such kits could include a plurality of scaffold shapes and sizes, suitable bone cements, as well as surgical tools, screws, shaping aids etc. which may be required to shape the scaffold before implanting, remove bone or otherwise be required during the surgery.

The description of the teachings is merely exemplary in nature and, thus, variations that do not depart from the gist of the teachings are intended to be within the scope of the teachings. Such variations are not to be regarded as a departure from the spirit and scope of the teachings.

The description of the teachings is merely exemplary in nature and, thus, variations that do not depart from the gist of the teachings are intended to be within the scope of the teachings. Such variations are not to be regarded as a departure from the spirit and scope of the teachings.

REFERENCES 1. de Boer H H. The history of bone grafts. Clin Orthop Relat Res 1988; 226:292-8.
2. Vacanti C A, Kim W, Upton J, Vacanti M P, Mooney D, Schloo B, et al. Tissue-engineered growth of bone and cartilage. Transplant Proc 1993; 25:1019-21.
3. Bonfiglio M, Jeter W S. Immunological responses to bone. Clin Orthop Relat Res 1972; 87:19-27.
4. Coombes A G, Meikle M C. Resorbable synthetic polymers as replacements for bone graft. Clin Mater 1994; 17:35-67.
5. Rizzi S C, Heath D J, Coombes A G, Bock N, Textor M, Downes S. Biodegradable polymer/hydroxyapatite composites: surface analysis and initial attachment of human osteoblasts. J Biomed Mater Res 2001; 55:475-86.
6. Laurencin C T, Attawia M, Borden M D. Advancements in tissue engineered bone substitutes. Curr Opin Orthop 1999; 10:445-51.
7. Ambrosio A M, Sahota J S, Khan Y, Laurencin C T. A novel amorphous calcium phosphate polymer ceramic for bone repair: I. Synthesis and characterization. J Biomed Mater Res 2001; 58: 295-301.
8. Marra K G, Szem J W, Kumta P N, DiMilla P A, Weiss L E. In vitro analysis of biodegradable polymer blend/hydroxyapatite composites for bone tissue engineering. J Biomed Mater Res 1999; 47:324-35.
9. Wang M. Developing bioactive composite materials for tissue replacement. Biomaterials 2003; 24:2133-51.
10. Van Landuyt P, Li F, Keustermans J P, Streydio J M, Delannay F, Munting E. The influence of high sintering temperatures on the mechanical properties of hydroxyapatite. J Mater Sci Mater Med 1995; 6:8-13.
11. Khan Y M, Katti D S, Laurencin C T. Novel polymer-synthesized ceramic composite-based system for bone repair: An in vitro evaluation. J Biomed Mater Res A 2004; 69:728-37.
12. Kikuchi M, Cho S-B, Suetsugu Y, Tanaka J. In vitro tests and in vivo tests developed TCP/CPLA composites. Bioceramics 1997; 10: 407-10.
13. Reis R L, Cunha A M, Fernandes M H, Correia R N. Bioinert and biodegradable polymeric matrix composites filled with bioactive $SiO_2$-$3CaO$◆$P_2O_5$-MgO glasses and glass-ceramics. Bioceramics 1997; 10:415-8.
14. Piattelli A, Franco M, Ferronato G, Santello M T, Martinetti R, Scarano A. Resorption of composite polymer-hydroxyapatite membranes: a time-course study in rabbit. Biomaterials 1997; 18: 629-33.
15. Lu L, Currier B L, Yaszemski M J. Synthetic bone substitutes. Curr Opin Orthop 2000; 11:383-90.
16. Peter S J, Lu L, Kim D J, Mikos A G. Marrow stromal osteoblast function on a poly(propylene fumarate)/beta-tricalcium phosphate biodegradable orthopaedic composite. Biomaterials 2000; 21:1207-13.
17. Wei G, Ma P X. Structure and properties of nano-hydroxyapatite/polymer composite scaffolds for bone tissue engineering. Biomaterials 2004; 25:4749-57.
18. Guan L, Davies J E. Preparation and characterization of a highly macroporous biodegradable composite tissue engineering scaffold. J Biomed Mater Res A 2004; 71:480-7.
19. Zhang R, Ma P X. Poly(alpha-hydroxyl acids)/hydroxyapatite porous composites for bone-tissue engineering. I. Preparation and morphology. J Biomed Mater Res 1999; 44:446-55.
20. Lee S H, Kim B S, Kim S H, Kang S W, Kim Y H. Thermally produced biodegradable scaffolds for cartilage tissue engineering. Macromol Biosci 2004; 4:802-10.
21. Yang S, Leong K F, Du Z, Chua C K. The design of scaffolds for use in tissue engineering. Part I. Traditional factors. Tissue Eng 2001; 7:679-89.
22. Jung Y, Kim S S, Kim Y H, Kim S H, Kim B S, Kim S, et al. A poly(lactic acid)/calcium metaphosphate composite for bone tissue engineering. Biomaterials 2005; 26:6314-22.
23. Jung Y, Kim S H, Kim S S, You H J, Kim B S, Kim S, et al. Tissue engineered bone formation with polymer/ceramic composites by press-and-baking method. Key Eng Mater 2005; 288:79-82.
24. Harris L D, Kim B S, Mooney D J. Open pore biodegradable matrices formed with gas foaming J Biomed Mater Res 1998; 42: 396-402.
25. Cho S W, Kim I K, Lim S H, Kim D I, Kang S W, Kim S H, et al. Smooth muscle-like tissues engineered with bone marrow stromal cells. Biomaterials 2004; 25:2979-86.

26. Cho S W, Kim S S, Rhie J W, Cho H M, Choi C Y, Kim B S. Engineering of volume-stable adipose tissues. Biomaterials 2005; 26: 3577-85.
27. Kim B S, Jeong S I, Cho S W, Nikolovski J, Mooney D J, Lee S H, et al. Tissue engineering of smooth muscle under a mechanically dynamic condition. J Microbiol Biotech 2003; 13:841-5.
28. Whitson S W, Whitson M A, Bowers Jr. D E, Falk M C. Factors influencing synthesis and mineralization of bone matrix from fetal bovine bone cells grown in vitro. J Bone Miner Res 1992; 7:727-41.
29. Ekholm M, Hietanen J, Tulamo R M, Muhonen J, Lindqvist C, Kellomaki M, et al. Tissue reactions of subcutaneously implanted mixture of epsilon-caprolactone-lactide copolymer and tricalcium phosphate. An electron microscopic evaluation in sheep. J Mater Sci Mater Med 2003; 14:913-8.
30. Jaiswal N, Haynesworth S E, Caplan A I, Bruder S P. Osteogenic differentiation of purified, culture-expanded human mesenchymal stem cells in vitro. J Cell Biochem 1997; 64:295-312.
31. Lewandrowski K U, Bondre S P, Wise D L, Trantolo D J. Enhanced bioactivity of a poly(propylene fumarate) bone graft substitute by augmentation with nano-hydroxyapatite. Biomed Mater Eng 2003; 13:115-24.
32. Ginebra M P, Driessens F C, Planell J A. Effect of the particle size on the micro and nanostructural features of a calcium phosphate cement: a kinetic analysis. Biomaterials 2004; 25: 3453-62.
33. Burg K J L, Porter S, Kellam J F. Biomaterial Developments for bone tissue engineering. Biomaterials 2000; 21:2347-2359.
34. Akoa M, Aoki H, Kato K. Mechanical properties of sintered hydroxyapatite for prosthetic applications. J Mater Sci 1981; 16:809-812.
35. Anselme K. Osteoblast adhesion on biomaterials. Biomaterials 2000; 21:667-681.
36. Howe A K, Aplin A E, Juliano R L. Anchorage-dependent ERK signaling-mechanisms and consequences. Curr Opin Genet Dev 2002; 12:30-35.
37. Bigi A, Boanini E, Panzavolta S, Roveri N, Rubini K. Bone like apatite growth on hydroxyapatite-gelatin sponges from simulated body fluid. J Biomed Mater Res 2002; 59:709-715.
38. Stupp S I, Ciegler G W. Organoapatites: Materials for artificial bone. I. Synthesis and microstructure. J Biomed Mater Res 1992; 26:169-183.
39. Vandiver J, Dean D, Patel N, Bonfield W, Ortiz C. Nanoscale variation in surface charge of synthetic hydroxyapatite detected by chemically and spatially specific high-resolution force spectroscopy. Biomaterials 2005; 26:271-283.
40. Lu H H, El-Amin S F, Scott K D, Laurencin C T. Three-dimensional, bioactive, biodegradable, polymer-bioactive glass composite scaffolds with improved mechanical properties support collagen synthesis and mineralization of human osteoblast-like cells in vitro. J Biomed Mater Res A 2003; 64: 465-474.
41. Li H, Chang J. Preparation and characterization of bioactive and biodegradable wollastonite/poly(D,L-lactic acid) composite scaffolds. J Mater Sci Mater Med 2004; 15:1089-1095.

What is claimed is:

1. A bone graft biomaterial comprised of a scaffold consisting of a biocompatible polymer and a bioceramic composite in a ratio of about 1:2 to about 2:1 wherein the bioceramic particles are less than 1.0 μm in diameter and wherein the scaffolds contain interconnected pores made via a gas foaming or a particulate leaching process, wherein the bioceramic particles are exposed on the surface of the biomaterial and wherein the biomaterial is impregnated with collagen after the pores are formed by forcing the collagen into the pores by placing the scaffold into a collagen solution and the solution is placed under a vacuum until the temperature is just above the freezing point of the collagen solution, the solution allowed to warm before being subjected to repeated cycles of vacuum and warming.

2. The bone graft material of claim 1 wherein the biocompatible polymer is selected from the group comprising Poly lactic acid (PLA), poly glycolic acid (PGA), Poly lactic co-glycolic acid (PLGA), and copolymers with polyethylene glycol (PEG); polyanhydrides, poly(ortho)esters, polyurethanes, poly(butyric acid), poly(valeric acid), poly(lactide-co-caprolactone) and trimethylene carbonate and combinations and co-polymers thereof.

3. The bone graft material of claim of claim 1 wherein the bioceramic is selected from the group consisting of hydroxyapatite, tricalcium phosphate, bioglass, calcium phosphate or bone or a combination thereof.

4. The bone graft material of claim 3 where in the bioceramic particles are a mixture of hydroxy apatite and TCP in a ratio of about 40:60.

5. The bone graft material of claim 1 wherein the bioceramic particles are from 100 nm to 1000 nm in diameter.

6. The bone graft material of claim 5 wherein the bioceramic particles are from 100 nm to 400 nm in diameter.

7. The bone graft material of claim 1 wherein the biocompatible polymer is poly lactic acid, poly glycolic acid, lactide or caprolactone or copolymers or combinations thereof.

8. The bone graft material of claim 7 comprising two polymers in a ratio from 2:1 to 1:2.

9. The bone graft material of claim 7 where the polymers are lactide and caprolactone in a ratio of about 75:25 by weight.

10. A bone graft biomaterial of claim 1 wherein the bioceramic is TCP coated hydroxyapatite.

11. The bone graft material of claim 1 wherein the ratio of biocompatible polymer to bioceramic ranges from about 80:20 to about 50:50.

12. The bone graft material of claim 11 wherein the ratio of polymer to bioceramic is about 60:40.

13. A bone graft material comprising lactide and caprolactone polymers in a ratio from about 1:2 to about 2:1 which are in a ratio of from about 80:20 to about 50:50 with a bioceramic having a diameter from about 150 microns to about 300 microns comprising hydroxyapatite, TCP, hydroxyapatite TCP or a mixture thereof wherein the scaffold is formed via gas foaming.

14. The bone graft material of claim 13 where in the ratio of lactide to caprolactone is 75:25.

15. The bone graft material of claim 13 wherein the ratio of lactide and caprolactone polymers to bioceramic is about 60:40.

* * * * *